(12) United States Patent
Iddan et al.

(10) Patent No.: US 7,801,584 B2
(45) Date of Patent: Sep. 21, 2010

(54) PANORAMIC FIELD OF VIEW IMAGING DEVICE

(75) Inventors: Gavriel J. Iddan, Haifa (IL); Daphna Levy, Carmiel (IL); Kevin Rubey, Ventura, CA (US); Mordechai Frisch, Moreshet (IL)

(73) Assignee: Given Imaging Ltd., Yoqneam (IL)

( * ) Notice: Subject to any disclaimer, the term of this patent is extended or adjusted under 35 U.S.C. 154(b) by 601 days.

(21) Appl. No.: 10/555,350

(22) PCT Filed: May 2, 2004

(86) PCT No.: PCT/IL2004/000367

§ 371 (c)(1),
(2), (4) Date: Nov. 1, 2005

(87) PCT Pub. No.: WO2004/096008

PCT Pub. Date: Nov. 11, 2004

(65) Prior Publication Data

US 2006/0052708 A1     Mar. 9, 2006

Related U.S. Application Data

(60) Provisional application No. 60/466,729, filed on May 1, 2003.

(51) Int. Cl.
*A61B 5/00* (2006.01)
(52) U.S. Cl. .................. 600/407; 600/160; 600/170; 600/178; 600/476
(58) Field of Classification Search .................. 600/109, 600/160, 170, 178, 302, 407, 473, 476, 176; 128/906; 348/65, 77
See application file for complete search history.

(56) References Cited

U.S. PATENT DOCUMENTS 3,683,389 A     8/1972     Hollis (Continued)

FOREIGN PATENT DOCUMENTS

AU     2004201212     10/1999

(Continued)

OTHER PUBLICATIONS

U.S. Appl. No. 10/493,751, filed Apr. 27, 2004, Glukhovsky et al.

(Continued)

*Primary Examiner*—Brian Casler
*Assistant Examiner*—Jonathan G Cwem
(74) *Attorney, Agent, or Firm*—Pearl Cohen Zedek Latzer, LLP

(57) ABSTRACT

An in vivo imaging device with a curved reflective element and for example a concave portion of an outer shell of such device. Such curved reflective element may for example reflect onto an image sensor light rays from an object where such light rays before reflection are substantially parallel to the plane of the image sensor. An in vivo imaging device with a reflective surface situated at an angle to an image sensor of such imaging device. Such an angle may be for example a 45 degree angle so that light rays that are substantially parallel to a plain of an image sensor of an imaging device may for example be reflected by the reflective surface onto the image sensor.

12 Claims, 13 Drawing Sheets

U.S. PATENT DOCUMENTS

| | | | |
|---|---|---|---|
| 3,705,579 A | 12/1972 | Morini et al. |
| 3,971,362 A | 7/1976 | Pope et al. |
| 4,027,510 A | 6/1977 | Hiltebrandt |
| 4,198,960 A | 4/1980 | Utsugi |
| 4,217,045 A | 8/1980 | Ziskind |
| 4,278,077 A | 7/1981 | Mizumoto |
| 4,481,952 A | 11/1984 | Pawelec |
| 4,588,294 A | 5/1986 | Siegmund |
| 4,642,678 A | 2/1987 | Cok |
| 4,689,621 A | 8/1987 | Kleinberg |
| 4,741,327 A | 5/1988 | Yabe |
| 4,782,819 A | 11/1988 | Adair |
| 4,819,620 A | 4/1989 | Okutsu |
| 4,844,076 A | 7/1989 | Lesho et al. |
| 4,901,708 A | 2/1990 | Lee |
| 4,905,670 A | 3/1990 | Adair |
| 4,936,823 A | 6/1990 | Colvin et al. |
| 4,951,135 A | 8/1990 | Sasagawa et al. |
| 5,026,368 A | 6/1991 | Adair |
| 5,143,054 A | 9/1992 | Adair |
| 5,209,220 A | 5/1993 | Hiyama et al. |
| 5,279,607 A | 1/1994 | Schentag et al. |
| 5,331,551 A | 7/1994 | Tsuruoka et al. |
| 5,368,015 A | 11/1994 | Wilk |
| 5,373,322 A | 12/1994 | Laroche et al. |
| 5,379,757 A | 1/1995 | Hiyama et al. |
| 5,381,784 A | 1/1995 | Adair |
| 5,382,976 A | 1/1995 | Hibbard |
| 5,398,670 A | 3/1995 | Ortiz et al. |
| 5,459,605 A | 10/1995 | Kempf |
| 5,506,619 A | 4/1996 | Adams, Jr. et al. |
| 5,603,687 A | 2/1997 | Hori et al. |
| 5,604,531 A | 2/1997 | Iddan et al. |
| 5,607,435 A | 3/1997 | Sachdeva et al. |
| 5,652,621 A | 7/1997 | Adams, Jr. et al. |
| 5,653,677 A | 8/1997 | Okada et al. |
| 5,662,587 A | 9/1997 | Grundfest et al. |
| 5,697,384 A | 12/1997 | Miyawaki et al. |
| 5,819,736 A | 10/1998 | Avny et al. |
| 5,940,126 A | 8/1999 | Kimura |
| 5,993,378 A | 11/1999 | Lemelson |
| 6,123,666 A | 9/2000 | Wrenn et al. |
| 6,184,922 B1 | 2/2001 | Saito et al. |
| 6,184,923 B1 | 2/2001 | Miyazaki |
| 6,240,312 B1 | 5/2001 | Alfano et al. |
| D457,236 S | 5/2002 | Meron et al. |
| 6,428,469 B1 | 8/2002 | Iddan et al. |
| 6,453,199 B1 | 9/2002 | Kobozev |
| 6,632,175 B1 | 10/2003 | Marshall |
| 6,709,387 B1 | 3/2004 | Glukhovsky et al. |
| D492,791 S | 7/2004 | Alexander |
| 6,918,872 B2 | 7/2005 | Yokoi et al. |
| 6,934,573 B1 | 8/2005 | Glukhovsky et al. |
| 6,950,690 B1 | 9/2005 | Meron et al. |
| D512,150 S | 11/2005 | Iddan et al. |
| 7,039,453 B2 * | 5/2006 | Mullick et al. ............. 600/476 |
| 2001/0017649 A1 | 8/2001 | Yaron |
| 2001/0051766 A1 | 12/2001 | Gazdzinski |
| 2002/0032366 A1 | 3/2002 | Iddan et al. |
| 2002/0042562 A1 | 4/2002 | Meron et al. |
| 2002/0103417 A1 | 8/2002 | Gazdzinski |
| 2002/0107444 A1 | 8/2002 | Adler |
| 2002/0109774 A1 | 8/2002 | Meron et al. |
| 2002/0177779 A1 | 11/2002 | Adler et al. |
| 2002/0198439 A1 | 12/2002 | Mizuno |
| 2003/0018280 A1 | 1/2003 | Lewkowicz et al. |
| 2003/0028078 A1 | 2/2003 | Glukhovsky |
| 2003/0043263 A1 | 3/2003 | Glukhovsky et al. |
| 2003/0045790 A1 | 3/2003 | Lewkowicz et al. |
| 2003/0073935 A1 | 4/2003 | Segawa et al. |
| 2003/0077223 A1 | 4/2003 | Glukhovsky et al. |
| 2003/0114742 A1 | 6/2003 | Lewkowicz et al. |
| 2003/0117491 A1 | 6/2003 | Avni et al. |
| 2003/0120130 A1 | 6/2003 | Glukhovsky et al. |
| 2003/0151661 A1 | 8/2003 | Davidson et al. |
| 2003/0167000 A1 | 9/2003 | Mullick et al. |
| 2003/0171648 A1 | 9/2003 | Yokoi et al. |
| 2003/0171649 A1 | 9/2003 | Yokoi et al. |
| 2003/0195415 A1 | 10/2003 | Iddan |
| 2003/0208107 A1 | 11/2003 | Refael |
| 2003/0214579 A1 | 11/2003 | Iddan |
| 2003/0214580 A1 | 11/2003 | Iddan |
| 2003/0216622 A1 | 11/2003 | Meron et al. |
| 2004/0027459 A1 | 2/2004 | Segawa et al. |
| 2004/0027500 A1 | 2/2004 | Davidson et al. |
| 2004/0073087 A1 | 4/2004 | Glukhovsky et al. |
| 2004/0087832 A1 | 5/2004 | Glukhovsky et al. |
| 2004/0138532 A1 | 7/2004 | Glukhovsky |
| 2004/0171914 A1 | 9/2004 | Avni |
| 2004/0199061 A1 | 10/2004 | Glukhovsky |
| 2004/0236182 A1 | 11/2004 | Iddan et al. |
| 2004/0254455 A1 | 12/2004 | Iddan |
| 2004/0258328 A1 | 12/2004 | Adler |
| 2005/0025368 A1 | 2/2005 | Glukhovsky |
| 2005/0043586 A1 | 2/2005 | Suzushima |
| 2005/0049461 A1 | 3/2005 | Honda et al. |
| 2006/0015013 A1 | 1/2006 | Gilad et al. |

FOREIGN PATENT DOCUMENTS

| | | |
|---|---|---|
| DE | 3440177 | 5/1986 |
| EP | 0 228 493 | 7/1987 |
| IL | 143259 | 5/2001 |
| JP | 57-45833 | 3/1982 |
| JP | 58-29439 | 2/1983 |
| JP | 3-289779 | 12/1991 |
| JP | 4-109927 | 4/1992 |
| JP | 4-180736 | 6/1992 |
| JP | 5015515 | 1/1993 |
| JP | H 05-040231 | 2/1993 |
| JP | 6-285044 | 10/1994 |
| JP | 7-289504 | 11/1995 |
| JP | 2000-342522 | 12/2000 |
| JP | 2000-342527 | 12/2000 |
| JP | 2001-137182 | 5/2001 |
| JP | 2001-224551 | 8/2001 |
| JP | 2001-224553 | 8/2001 |
| JP | 2000-342524 | 6/2002 |
| JP | 2000-342525 | 6/2002 |
| JP | 2002-233494 | 8/2002 |
| JP | 2002-262200 | 9/2002 |
| WO | WO 92/21307 | 12/1992 |
| WO | WO 96/37796 | 11/1996 |
| WO | WO 98/11816 | 3/1998 |
| WO | WO 98/51993 | 11/1998 |
| WO | WO 00/22975 | 4/2000 |
| WO | WO 00/76391 | 12/2000 |
| WO | WO 01/08548 | 2/2001 |
| WO | WO 01/50180 | 7/2001 |
| WO | WO 01/50941 | 7/2001 |
| WO | WO 01/65995 | 9/2001 |
| WO | WO 02/26103 | 4/2002 |
| WO | WO 02/054932 | 7/2002 |
| WO | WO 02/067593 | 8/2002 |
| WO | WO 02/094337 | 11/2002 |
| WO | WO 02/102224 | 12/2002 |
| WO | WO 03/003706 | 1/2003 |
| WO | WO 03/011103 | 2/2003 |
| WO | WO 03/053241 | 7/2003 |
| WO | WO 2004/028336 | 4/2004 |
| WO | WO 2004/082472 | 9/2004 |
| WO | WO 2004/088448 | 10/2004 |

| | | |
|---|---|---|
| WO | WO 2004/096008 | 11/2004 |

OTHER PUBLICATIONS

U.S. Appl. No. 10/166,025, filed Jun. 11, 2002, Lewkowicz et al.
U.S. Appl. No. 10/493,751, Apr. 27, 2004, Glukhovsky et al.
U.S. Appl. No. 10/213,345, filed Aug. 7, 2002, Glukhovsky.
The Radio Pill, Rowlands, et al., British Communications and Electronics, Aug. 1960, pp. 598-601.
Wellesley Company Sends Body Monitors Into Space—Crum, Apr. 1998.
Wireless Transmission of a Color Television Moving Image From the Stomach Using a Miniature CCD Camera, Light Source and Microwave Transmitter, Swain CP, Gong F, Mills TN. Gastrointest Endosc 1997; 45:AB40.
BBC News Online—Pill Camera to "Broadcast From the Gut", Feb. 21, 2000, www.news.bbc.co.uk.
Biomedical Telemetry, R. Stewart McKay, Published by John Wiley and Sons, 1970.
R. Kimmel, "Demosaicing: Image reconstruction from color ccd samples", IEEE Transactions on Image Processing, vol. 8, pp. 1221-1228, 1999.
D. D. Muresan and T.W. Parks, "Optimal Recovery approach to image interpolation", in IEEE Proc. ICIP., vol. 3, 2001 pp. 7-10.
Shin-ishi et al.,"Robots for the future", pp. 1-2, Nov. 29, 2001 jp/nipponia/nipponia13/sp05.html.
Video camera to "Take", RF System Lab, 1 page, Dec. 25, 2001.
Norkia3, RF Systems Lab, pp. 1-14, http://www.rfnorika.com/, Jan. 1, 2002.
B. Guntruck, Y. Altunbasak and R. Mersereau, "Color plane interpolation using alternating projections", IEEE Transactions on Image Processing, vol. 11, No. 9 Sep. 2002, pp. 997-1013.
Wang et al., "Integrated Micro-Instrumentation for Dynamic Monitoring of the Gastro-Intestinal Tract", www.see.ed.ac.uk/Naa Publications.html, presented at IEEE Instrumentation and Measurement Technology Conference, May 2002, Anchorage, AK, USA, pp. 1-4.
Dan Slater, Panoramic Photography with Fisheye Lenses, © 1995, Published in the IAPP Journal 1996.
International Search Report for PCT/IL04/00367, mailed on Jun. 29, 2005.
Zachary Turke, New Smart Plastic Has Good Memory. EMDM Sep. 2001—reference attached.
Office Action of JP Application No. 507617/2006 mailed on Jan. 5, 2010.

* cited by examiner

PANORAMIC FIELD OF VIEW IMAGING DEVICE

CROSS-REFERENCE TO RELATED APPLICATIONS

This application is a National Phase Application of PCT International Application Number PCT/IL2004/000367, International Filing Date May 2, 2004, entitled "Panoramic Field of View Imaging Device", which in turn claims priority and benefit of U.S. Provisional Patent Application No. 60/466,729, filed May 1, 2003, entitled "Device, System and Method of Broad Field-Of-View Imaging", both of which are incorporated herein by reference in their entirety.

FIELD OF THE INVENTION

The invention relates to an in-vivo imaging device, method and system, typically for obtaining a panoramic or circular (360°) field of view.

BACKGROUND OF THE INVENTION

Devices and methods for performing in-vivo imaging of passages or cavities within a body, and for gathering information other than or in addition to image information (e.g., temperature information, pressure information), are known in the art. Such devices may include, inter alia, various endoscopic imaging systems and devices for performing imaging in various internal body cavities.

An in-vivo imaging device may include, for example, an imaging system for obtaining images from inside a body cavity or lumen, such as the GI tract. The imaging system may include, for example, an imager associated with an optical system, and optionally an illumination unit, a transmitter and an antenna. Other types of in-vivo devices exist, such as endoscopes which may not require a transmitter, and devices performing functions other than imaging.

Some in-vivo imaging devices have a limited or forward-looking field-of-view. Some desirable portions of an in-vivo lumen may not be imaged with such fields of view.

SUMMARY OF THE INVENTION

Embodiments of the invention provide an in-vivo imaging device, method or system that includes a reflective element, which may in some embodiments be curved or have a non-flat shape. In some embodiments the curved reflective element is to reflect onto an image sensor in such device light rays from an object, where such light rays are, before being reflected, substantially parallel to a plane of such image sensor that detects light.

In some embodiments, the image sensor may capture panoramic or partially panoramic images of an in-vivo area. Such view may for example approximate a ring shaped slice of a body lumen. The imaging device may for example include illumination units that may for example be arranged around an inside perimeter of the device. In some embodiments, illumination devices may be situated on an outward facing ring such that such illumination units are directed outwards from an imaging device. In some embodiments, light may be generated by a source external to the imaging device. In some embodiments, the device may include a concave, tapered, narrowed shaped portion such that the device takes on a "peanut" like shape. In some embodiments, such narrowed or concave portion may include a transparent ring around an outer shell of the device.

Embodiments of the invention provide an in-vivo imaging device with a reflective surface that may be situated for example at an angle such as for example a 45 degree angle to the plane of an image sensor of the imaging device. In some embodiments, the reflective surface may reflect light rays onto an image sensor where such light rays before reflection were substantially parallel to the plane of the image sensor upon which the light detection sensors are located. In some embodiments the reflective surface may be rotated by for example a motor and may provide a panoramic or partially panoramic field of view of a body lumen. Illumination of a body lumen may for example be synchronized with such rotation and may for example provide homogenous illumination of an in-vivo area. Such rotation may for example be at a variable rate. In some embodiments the field of view may include an area substantially perpendicular to the imaging device and an area in front of or behind the imaging device.

In some embodiments a panoramic image may be flattened for example into a rectangular image and may be displayed for example on an external display system.

Embodiments of the invention provide, for example, an in-vivo imaging device able to view and/or capture images of body areas transverse and/or substantially transverse to the general direction of movement of the in-vivo imaging device.

Embodiments of the invention further provide a method and a system for using such an in-vivo imaging device.

BRIEF DESCRIPTION OF THE DRAWINGS

The subject matter regarded as the invention is particularly pointed out and distinctly claimed in the concluding portion of the specification. The invention, however, both as to organization and method of operation, together with objects, features and advantages thereof, may best be understood by reference to the following detailed description when read with the accompanied drawings in which:

Figure 1:
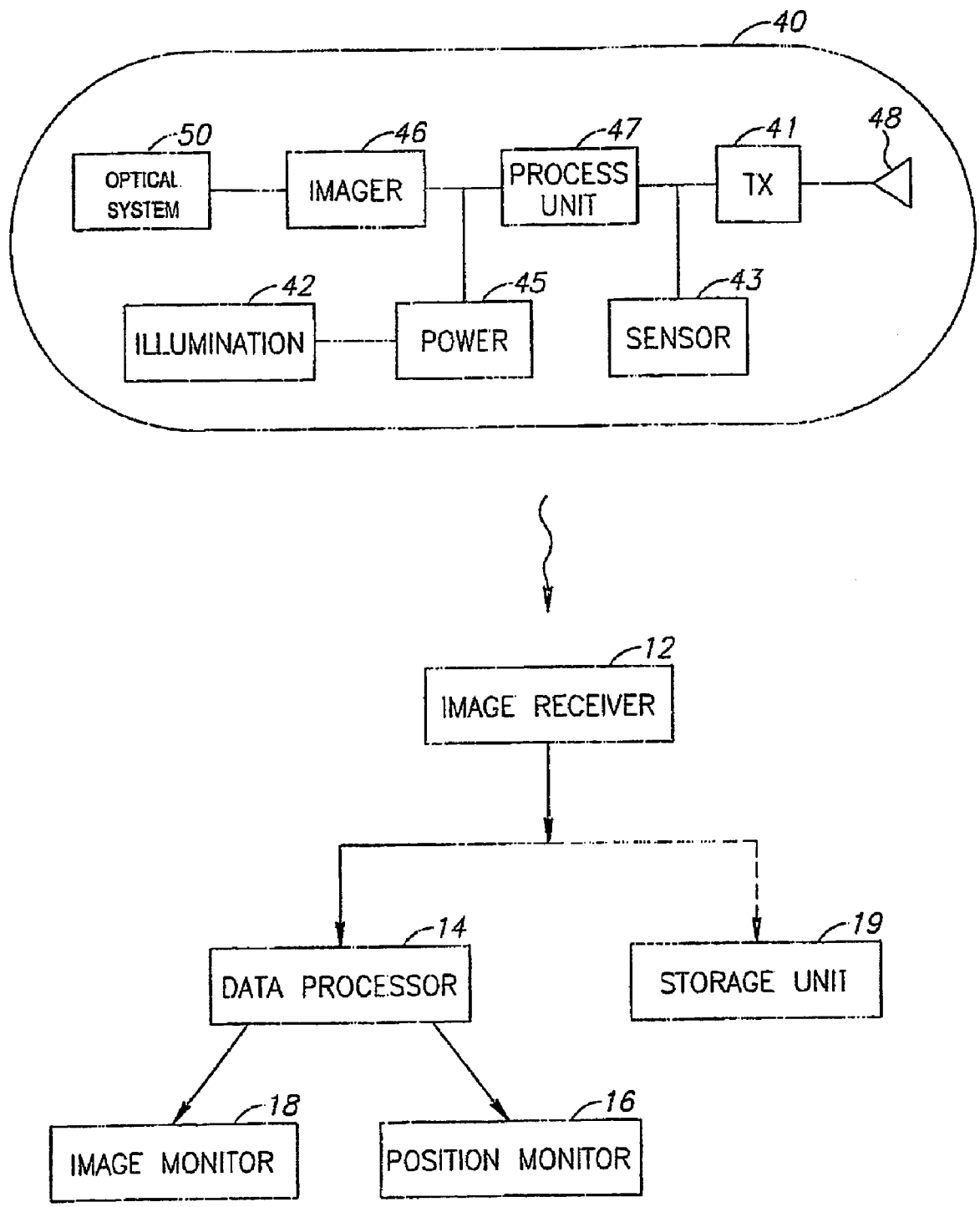
FIG. 1 is a schematic illustration of an in-vivo imaging system in accordance with embodiments of the invention.

It will be appreciated that for simplicity and clarity of illustration, elements shown in the figures have not necessarily been drawn to scale. For example, the dimensions of some of the elements may be exaggerated relative to other elements for clarity. Further, where considered appropriate, reference numerals may be repeated among the figures to indicate corresponding or analogous elements.

DETAILED DESCRIPTION OF THE INVENTION

In the following description, various aspects of the invention will be described. For purposes of explanation, specific configurations and details are set forth in order to provide a thorough understanding of the invention. However, it will also be apparent to one skilled in the art that the invention may be practiced without the specific details presented herein. Furthermore, well known features may be omitted or simplified in order not to obscure the invention.

It is noted that some embodiments of the present invention are directed to a typically swallowable in-vivo device. Other embodiments need not be swallowable. Devices according to embodiments of the present invention may be similar to embodiments described in International Application WO 01/65995 and/or in U.S. Pat. No. 5,604,531, each of which are assigned to the common assignee of the present invention and each of which are hereby fully incorporated by reference. Furthermore, a receiving and/or display system suitable for use with embodiments of the present invention may also be similar to embodiments described in WO 01/65995 and/or in U.S. Pat. No. 5,604,531. Of course, devices and systems as described herein may have other configurations and other sets of components.

Alternate embodiments of the device, system and method according to various embodiments of the invention may be used with other devices, non-imaging and/or non-in-vivo devices.

Reference is made to FIG. 1, which shows a schematic diagram of an embodiment of an in-vivo imaging system. In one embodiment, the system may include a device 40 having an imager 46, an illumination source 42, and a transmitter 41. In some embodiments, device 40 may be implemented using a swallowable capsule, but other sorts of devices or suitable implementations may be used. Outside the patient's body may be an image receiver 12 (typically including an antenna or an antenna array 48), a storage unit 19, a data processor 14, an image monitor 18, and a position monitor 16. While FIG. 1 shows separate monitors, in some embodiments, both an image and its position may be presented using a single monitor. Other systems and methods of storing and/or displaying collected image data may be used.

Transmitter 41 typically operates using radio waves, but in some embodiments, such as those where the device 40 is or is included within an endoscope, transmitter 41 may transmit via, for example, wire.

Device 40 typically may be or include an autonomous swallowable imaging device such as fox example a capsule, but may have other shapes, and need not be swallowable or autonomous. In one embodiment, device 40 includes an in-vivo video camera which may capture and transmit images of the GI tract while the device passes through the GI lumen. Other lumens may be imaged.

Imager 46 in device 40 may be connected to transmitter 41 also located in device 40. Transmitter 41 may transmit images to image receiver 12, which may send the data to data processor 14 and/or to storage unit 19. Transmitter 41 may also include control capability, although control capability may be included in a separate component Transmitter 41 may include any suitable transmitter able to transmit images and/or other data (e.g., control data) to a receiving device. For example, transmitter 41 may include an ultra low power RF transmitter with high bandwidth input, possibly provided in Chip Scale Package (CSP). Transmitter 41 may transmit via antenna 48.

A system according to some embodiments of the invention includes an in-vivo sensing device transmitting information (e.g., images or other data) to a data receiver and/or recorder possibly close to or worn on a subject. A data receiver and/or recorder may of course take other suitable configurations. The data receiver and/or recorder may transfer the information received from a transmitter to a larger computing device, such as a workstation or personal computer, where the data may be further analyzed, stored, and/or displayed to a user. In other embodiments, each of the various components need not be required; for example, an internal device may transmit or otherwise transfer (e.g., by wire) information directly to a viewing or processing system.

In some embodiments, transmitter 41 may include, for example, a transmitter receiver or a transceivers to allow transmitter 41 to receive a transmission. Additionally or alternatively, a separate or integrated receiver (not shown) or transceiver (not shown) may be used within device 40, instead of transmitter 41 or in addition to it, to allow device 40 to receive a transmission. In one embodiment, device 40 and/or transmitter 41 may, for example, receive a transmission and/or data and/or signal which may include commands to device 40. Such commands may include, for example, a command to turn on or turn off device 40 or any of its components, a command instructing device 40 to release a material, e.g., a drug, to its environment, a command instructing device 40 to collect and/or accumulate a material from its environment, a command to perform or to avoid performing an operation which device 40 and/or any of its components are able to perform, or any other suitable command. In some embodiments, the commands may be transmitted to device 40, for example, using a pre-defined channel and/or control channel. In one embodiment, the control channel may be separate from the data channel used to send data from transmitter 41 to receiver 12. In some embodiments, the commands may be sent to device 40 and/or to transmitter 41 using receiver 12, for example, implemented using a transmitter-receiver and/or transceiver, or using a separate and/or integrated transmitter (not shown) or transceiver (not shown) in the imaging system of FIG. 1.

Power source 45 may include one or more batteries. For example, power source 45 may include silver oxide batteries, lithium batteries, other suitable electrochemical cells having a high energy density, or the like. Other power sources may be used. For example, instead of internal power source 45 or in addition to it, an external power source may be used to transmit power to device 40.

Data processor 14 may analyze the data and may be in communication with storage unit 19, transferring data such as frame data to and from storage unit 19. Data processor 14 may also provide the analyzed data to image monitor 18 and/or position monitor 16, where a user may view the data. In one embodiment, for example, image monitor 18 may present an image of the GI lumen, and position monitor 16 may present the position in the GI tract at which the image was taken. In one embodiment, data processor 14 may be configured for real time processing and/or for post processing to be performed and/or viewed at a later time. Other monitoring and receiving systems may be used in accordance with embodiments of the invention. Two monitors need not be used.

In some embodiments, in addition to revealing pathological conditions of the GI tract, the system may provide information about the location of these pathologies. Suitable tracking devices and methods are described in embodiments in the above mentioned U.S. Pat. No. 5,604,531 and/or U.S. Patent Application Publication No. US-2002-0173718-A1, filed May 20, 2002, titled "Array System and Method for Locating an In-Vivo Signal Source", assigned to the assignee of the present invention, and fully incorporated herein by reference.

It is noted that in embodiments of the invention, other location and/or orientation detection methods may be used. In one embodiment, the orientation information may include three Euler angles or quaternion parameters; other orientation information may be used. In one embodiment, location and/or orientation information may be determined by, for example, including two or more transmitting antennas in device 40, each with a different wavelength, and/or by detecting the location and/or orientation using a magnetic method. In some embodiments, methods such as those using ultrasound transceivers or monitors that include, for example, three magnetic coils that receive and transmit positional signals relative to an external constant magnetic field may be used. For example, device 40 may include an optional location device such as tracking and/or movement sensor 43 to indicate to an external receiver a location of the device 40.

Optionally, device 40 may include a processing unit 47 that processes signals generated by imager 46. Processing unit 47 need not be a separate component; for example, processing unit 47 may be integral to imager 46 or transmitter 41, and may not be needed.

Device 40 may include one or more illumination sources 42, for example one or more "white LEDs" or any other suitable light source, for illuminating the body lumen. In some embodiments, illumination sources 42 may provide, fox example, ultra-violet light, infra-red light, or any other desired light or spectral range. In one embodiment, illumination sources 42 may include a laser source and/or may provide one or more laser beams.

In some embodiments, an optional optical system 50, including, for example, one or more optical elements (not shown), such as one or more lenses or composite lens assemblies (not shown), one or more suitable optical filters (not shown), or any other suitable optical elements (not shown), may aid in focusing reflected light onto the imager 46 and performing other light processing. According to one embodiment optical system 50 includes a reflecting surface, such as a conical mirror.

Typically, device 40 transmits image information in discrete portions. Each portion typically corresponds to an image or frame. Other transmission methods are possible. For example, device 40 may capture an image once every half second, and, after capturing such an image, transmit the image to receiver 12. Other constant and/or variable capture rates and/or transmission rates may be used. Typically, the image data recorded and transmitted is digital color image data, although in alternate embodiments other image formats (e.g., black and white image data) may be used. In one embodiment, each frame of image data includes 256 rows of 256 pixels each, each pixel including data for color and brightness, according to known methods. For example, in each pixel, color may be represented by a mosaic of four sub-pixels, each sub-pixel corresponding to primaries such as red, green, or blue (where one primary is represented twice). The brightness of the overall pixel may be recorded by, for example, a one byte (i.e, 0-255) brightness value. Other data formats may be used.

In embodiments of the invention, device 40 and/or imager 46 may have a broad field of view. In some embodiments, device 40 and/or imager 46 may view and/or capture images of body areas transverse and/or substantially transverse to the general direction of movement of device 40. For example portions of body lumens directly adjacent to device 40, as opposed to in front of or behind the front and back (respectively) of device 40, may be imaged. Portions of body lumens between a forward and real end of the device may be imaged. Furthermore, in some embodiments, device 40 and/or imager 46 may view and/or capture panoramic images with a broad field-of-view, e.g., up to 360 degrees, and/or with a substantially circular or radial field-of-view.

In some embodiments, device 40 may be configured to have a forward-looking field-of-view and/or a transverse field-of-view, fox example, to produce a combined field-of-view having broad coverage both in line with device 40 and transverse thereto. In some embodiments, a transverse field-of-view may include in-vivo areas that are lying in planes that are perpendicular or substantially perpendicular to a plane of imager 46.

Embodiments of the invention may achieve a broad field-of-view, as detailed below. Some embodiments may use a reflective element, for example, a curved or other suitably shaped mirror, to capture a panoramic image. A mirror or reflective element need not be curved or shaped. Some embodiments may use a rotating mirror or reflective element to capture a panoramic image. A rotating mirror or reflective element need not be curved or shaped. In some embodiments, a plurality of imagers may be used to capture a broad field-of-view, for example, by placing multiple images such that they face different and/or overlapping directions. In some embodiments, a rotating imager may be used to capture a panoramic image. It is noted that while some exemplary embodiments are explained in detail herein, the invention is not limited in this regard, and other embodiments and/or implementations of a broad field-of-view imaging device are also within the scope of the invention.

Figure 2:
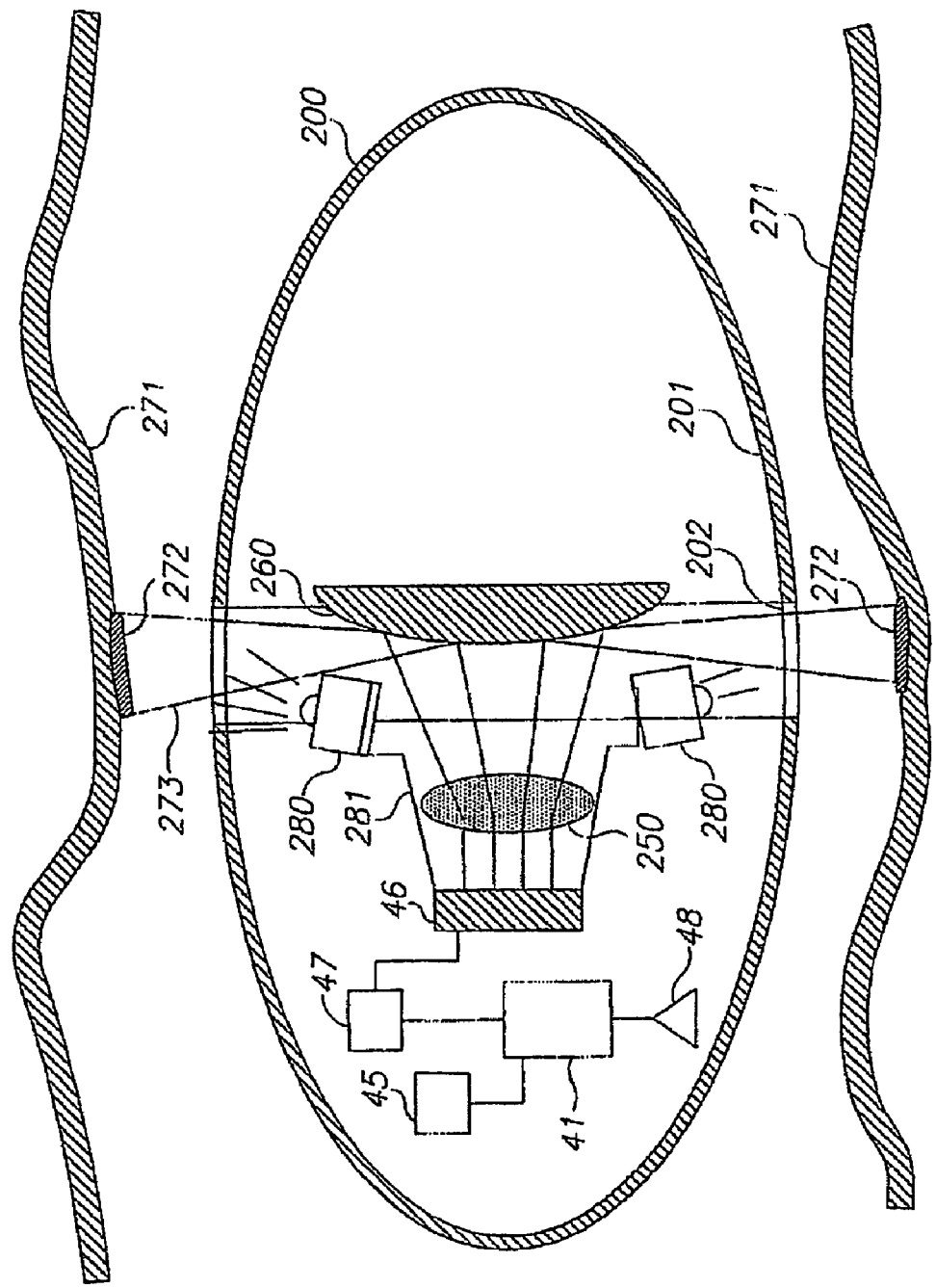
FIG. 2 is a schematic illustration of an in-vivo imaging device including a reflective element in accordance with embodiments of the invention.

FIG. 2 is a schematic illustration of an in vivo imaging device 200 in accordance with embodiments of the invention. Device 200 may be an implementation of variation of device 40, and may be used, fox example, in conjunction with the system of FIG. 1 or certain components of FIG. 1. For example, device 200 may be used in conjunction with receiver 12 and/or data processor 14. In one embodiment of the invention, device 200 may include a device 200, e.g., a capsule or other suitable device, imager 46, a processing unit 47, a transmitter 41, an antenna 48, a power source 45, a lens assembly 250, a reflective element 260, an illumination source (or plurality of sources) 280, and a holder 281. The processing capability of processing unit 47 may be combined with other units, such as transmitter 41 or a separate controller.

In one embodiment of the invention, device 200 may be a swallowable capsule. Device 200 may be partially or entirely transparent. For example, device 200 may include areas, such as a transparent ring 202, which are transparent and which allow components inside device 200 to have an un-obstructed field-of-view of the environment external to device 200. According to one embodiment transparent ring 202 is configured such that a 360 degree field of view is enabled. Other shaped transparent areas may be used.

Imager 46 may include an electronic imager for capturing images. For example, imager 46 may include a Complimentary Metal Oxide Semiconductor (CMOS) electronic imager including a plurality of elements. In embodiments of the invention, imager 46 may include other suitable types of optical sensors and/or devices able to capture images, such as a Charge-Coupled Device (CCD), a light-sensitive integrated circuit, a digital still camera, a digital video camera, or the like. It is noted that a CMOS imager is typically an ultra low power imager and may be provided in Chip Scale Packaging (CSP). Other types of CMOS imagers may be used.

Processing unit 47 may include any suitable processing chip or circuit able to process signals generated by imager 46.

For example, processing unit 47 may include a Central Processing Unit (CPU), a Digital Signal Processor (DSP), a microchip, a controller, any other suitable multi-purpose or specific processor, or any suitable combination of processors. It is noted that processing unit 47 and imager 46 may be implemented as separate components or as integrated components; for example, processing unit 47 may be integral to imager 46. Further, processing may be integral to imager 46 and/or to transmitter 41.

Lens assembly 250 may include, for example, one or more lenses or optical systems which may allow imager 46 to focus on an image reflected by reflective element 260. Additionally or alternatively, lens assembly 250 may include a combination of lenses able to zoom in and/or zoom out on an image or magnify one or more parts of an image reflected by reflective element 260. Lens assembly 250 may include one or more optical elements, for example, one or more lenses and/or optical filters, to allow or to aid focusing reflected light onto imager 46 and/or performing other light processing operations.

Reflective element 260 may include, for example, a curved mirror. In some embodiments, reflective element 260 may include, for example, a metallic element, a reflective plastic element, a reflective coated plastic element, or a glass element. Reflective element 260 may be shaped and/or contoured such that it allows light reflected from a slice 272 of a body lumen 271 to be reflected by reflective element 260, through lens assembly 250, onto imager 46. For example, reflective element 260 may be oval, spherical, radial, circular, ellipse-shaped, faceted, conical, etc. It is noted that in some embodiments, reflective element 260 may have a shape, size and/or dimensions to allow a desired reflection of light and/or to allow a desired range and/or field-of-view. In one embodiment, reflective element 260 may be manufactured using suitable optical design software and/or ray tracing software, for example, using "ZEMAX Optical Design Program" software. Other suitable shapes may be used.

Illumination source 280 may include one or more illumination sources or light sources to illuminate body lumen 271 and/or a slice 272 of body lumen 271. In one embodiment, illumination source 280 may include one or more Light-Emitting Diodes (LEDs), for example, one or more white LEDs. Such LEDs may be placed, aligned and/or positioned to allow a desired illumination of body lumen 271, for example, using a ring-shaped arrangement of LEDs able to illuminate body lumen 271 through transparent ring 202, that may for example be arranged around an inside perimeter of device 40. Other arrangements of illumination sources may be used in accordance with embodiments of the invention.

In some embodiments, an optional optical system (not shown) may be used in conjunction with illumination source 280, for example, to create a desired illumination, for example, homogenous illumination, of an imaged body lumen. In one embodiment, the optical system may include, for example, one or more mirrors and/or curved mirrors and/or lenses and/or reflective elements, shaped and/or positioned and/or aligned to create a desired, e.g., homogenous, illumination. For example, in one embodiment, the optical system may include a curved mirror, similar to reflective element 260. According to further embodiments an optical system may include filters.

Holder 281 may include a suitable structure to hold illumination sources 280. In some embodiments, holder 281 may be formed and/or shaped such that it reduces glare. In some embodiments, holder 281 may be formed and/or shaped such that it blocks stray light from reaching and/or flooding imager 46.

In one embodiment, as device 200 traverses body lumen 271, device 200 may capture images of a slice of body lumen 271, such as slice 272. Illumination source 280 may illuminate slice 272 of body lumen 271. The light from illuminated slice 272 may be reflected using reflective element 260, focused and/or transferred using lens assembly 250, and received by imager 46 which may thereby capture an image of slice 272. Before they are reflected by reflective element 260, the light rays 273 reflected back from an illuminated object or illuminated slice 272 in an in vivo area, may be parallel or substantially parallel to the plane of imager 46 or an image sensor of device 200 upon which the light detection sensors are located. In some embodiments the angle at which light rays 273 may strike reflective element 260 may depend on the size of transparent ring 202. Other factors such as for example the placement of illumination source 280 and the distance of a wall of body lumen 271 from device 200 may also influence the angle at which light rays 273 are reflected onto reflective element 260. In some embodiments, the curvature of reflective element 260 may be fashioned so that light rays 273 striking reflective element 260 at various angles are reflected towards imager 46. Such curvature may affect the range of angles of light rays 273 that may be reflected by reflective element 260 onto imager 46. In some embodiments the in-vivo area of which images may be captured may be substantially perpendicular to the plane of an image sensor.

In one embodiment, since device 200 may include transparent areas and/or portions, such as transparent ring 202, the captured image may include a reflected image of a ring-shaped slice 272 of body lumen 271. It is noted that lens assembly 250 may be configured, placed and/or aligned to filter and focus light from body lumen 271, such that only or substantially only light from a desired portion of body lumen 271, for example, a ring-shaped slice 27, falls on imager 46. Using device 200 may allow, for example, capturing a panoramic image of slice 272 of body lumen 271. Such panoramic image may include a substantially complete 360 degrees image of slice 272. Alternatively, if desired, such image may include a non-complete image of slice 272, for example, a 270 degrees image, a 210 degrees image, a 180 degrees image, or any other number of degrees between 0 and 360.

In one embodiment, the panoramic image of slice 272 may be ring-shaped. Such an image may be converted into a rectangular image of slice 272 or into other shapes. In one embodiment, the conversion may be performed, for example, by processing unit 47 before transmitting the image. Additionally or alternatively, the conversion may be performed by an external processor such as data processor 14 after receiving the transmitted image. The conversion may be performed, for example, using methods as known in the art to "flatten" a ring-shaped image into a rectangular image. The conversion may include other suitable operations for image manipulation and/or image enhancement, performed before and/or after transmission of the image by transmitter 41 to receiver 12. The conversion may be applied to one image, or to a group or a batch of sequential or non-sequential images.

Additionally or alternatively, images of slices of body lumen 271, such as slice 272, may be placed, aligned and/or combined together, for example, side by side, to create a combined image or several combined images from a plurality of images of slices 272. The combination of images of slices 272 may be performed, for example, by processing unit 47 and/or data processor 14. Additionally or alternatively, the combination of images of slices 272 may be performed before and/or after transmission of the image by transmitter 41 to receiver 12.

Figure 3A:
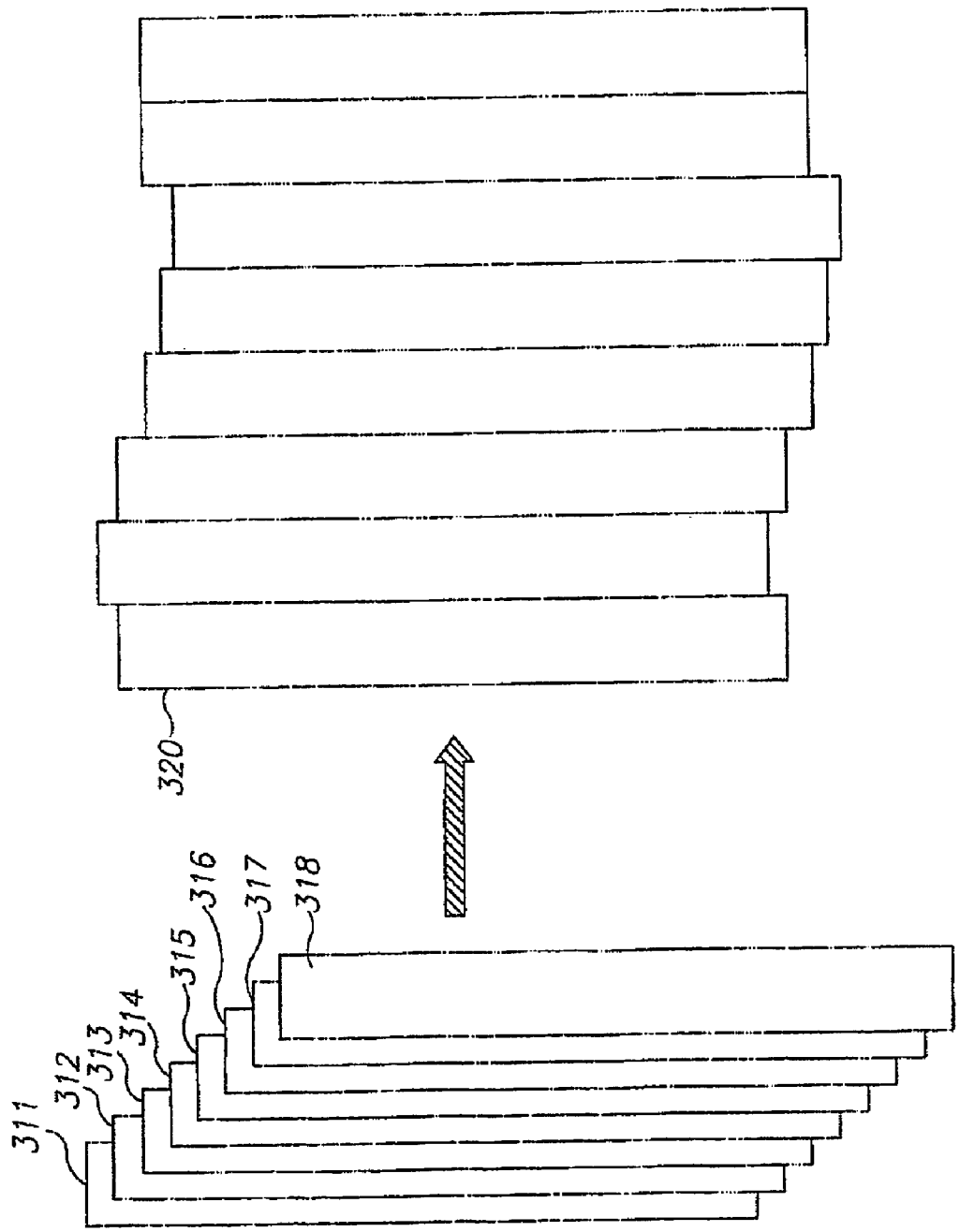
FIGS. 3A to 3E are schematic illustrations helpful to understanding some aspects of the operation of an in-vivo imaging device in accordance with embodiments of the invention.

FIG. 3A schematically illustrates the combination of a plurality of images of slices 311, 312, 313, 314, 315, 316, 317 and 318, into a combined image 320 in accordance with embodiments of the invention as described above.

Figure 3B:
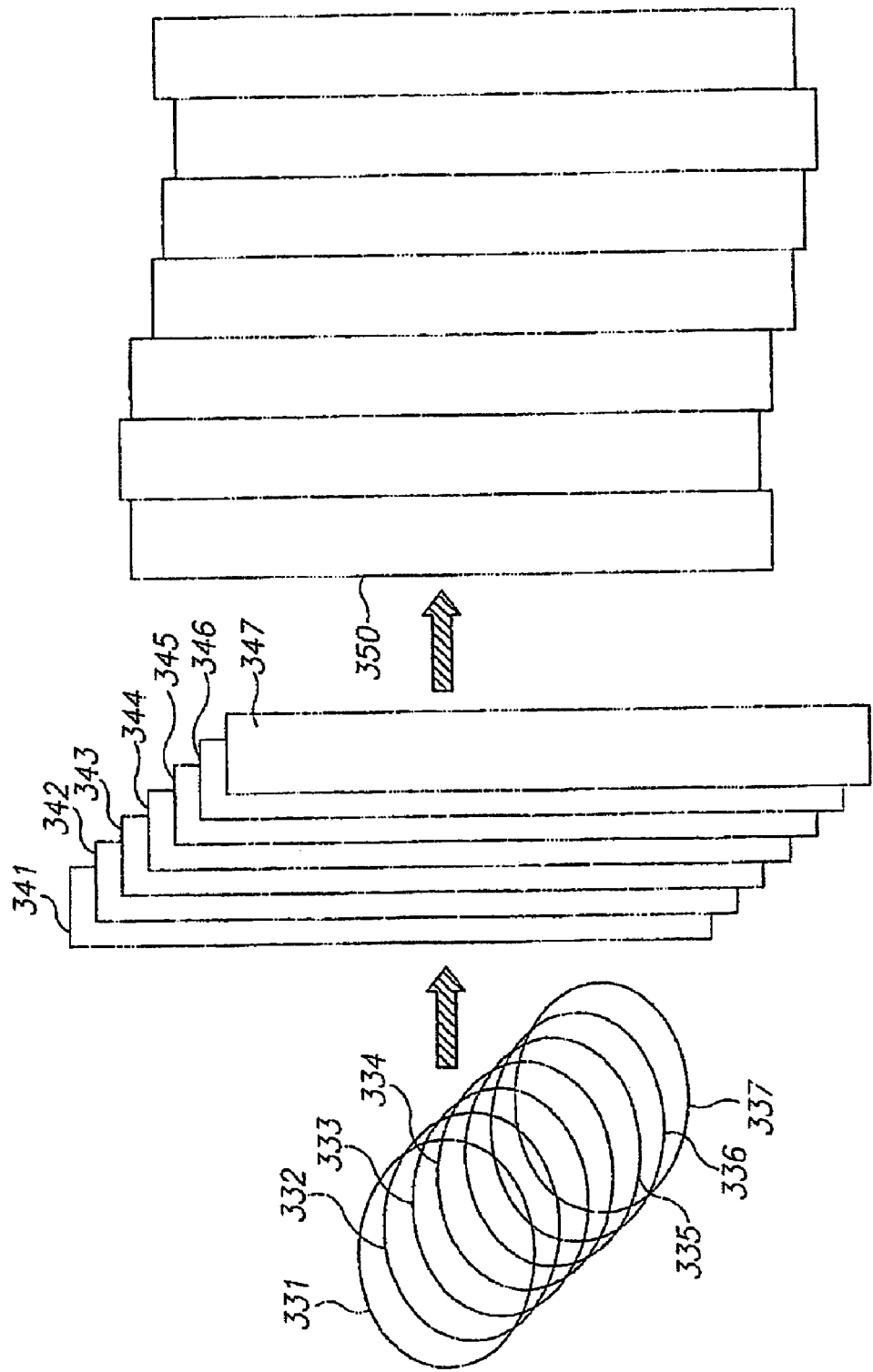

FIG. 3B schematically illustrates the conversion of a plurality of circular slice or ring shaped images 331, 332, 333, 334, 335, 336 and 337 into a plurality of rectangular images of slices 341, 342, 343, 344, 345, 346 and 347 in accordance with embodiments of the invention as described above. FIG. 3B further schematically illustrates the combination of a plurality of rectangular images of slices 341, 342, 343, 344, 345, 346 and 347 into a combined image 350 in accordance with embodiments of the invention as described above.

In some embodiments, imager 46 and/or device 40 may be controlled and/or programmed, for example, to allow capturing a continuous "chain of images" representing a body lumen. In one embodiment, consecutive images may partially cover one area of the body lumen, for example, such that images may partially overlap. In some embodiments, for example, image capture rate may be pre-defined and/or controlled in real-time, to allow imager 46 and/or device 40 to capture a continuous "chain of images". In one embodiment, a suitable image correlation technique may be used, for example, to detect and/or process overlapping areas among images, or to combine a plurality of images into a combined image.

Figure 3C:
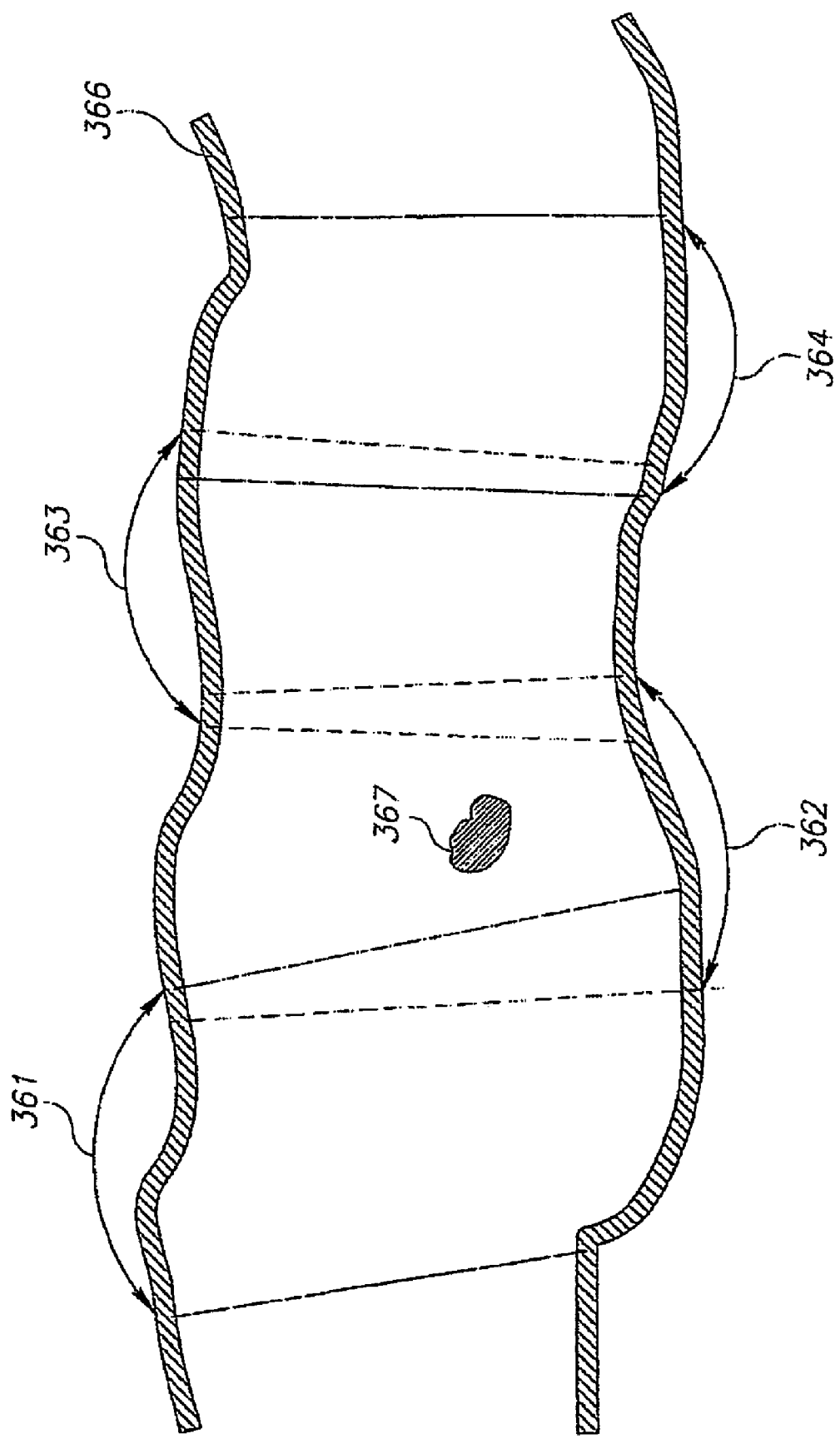

FIG. 3C schematically illustrates a "chain of images" of body lumen 366 in accordance with some embodiments of the invention. In one embodiment, images 361, 362, 363 and 364 may be captured by imager 46. As illustrated schematically in FIG. 3C, the images may partially overlap. For example, image 362 may include a portion of body lumen 366 captured in image 361 and/or a portion of body lumen 366 captured by image 363. Image 362 may additionally include an image of item 367, for example, a body organ, a material, a blood, a pathology, etc.

Figure 3D:
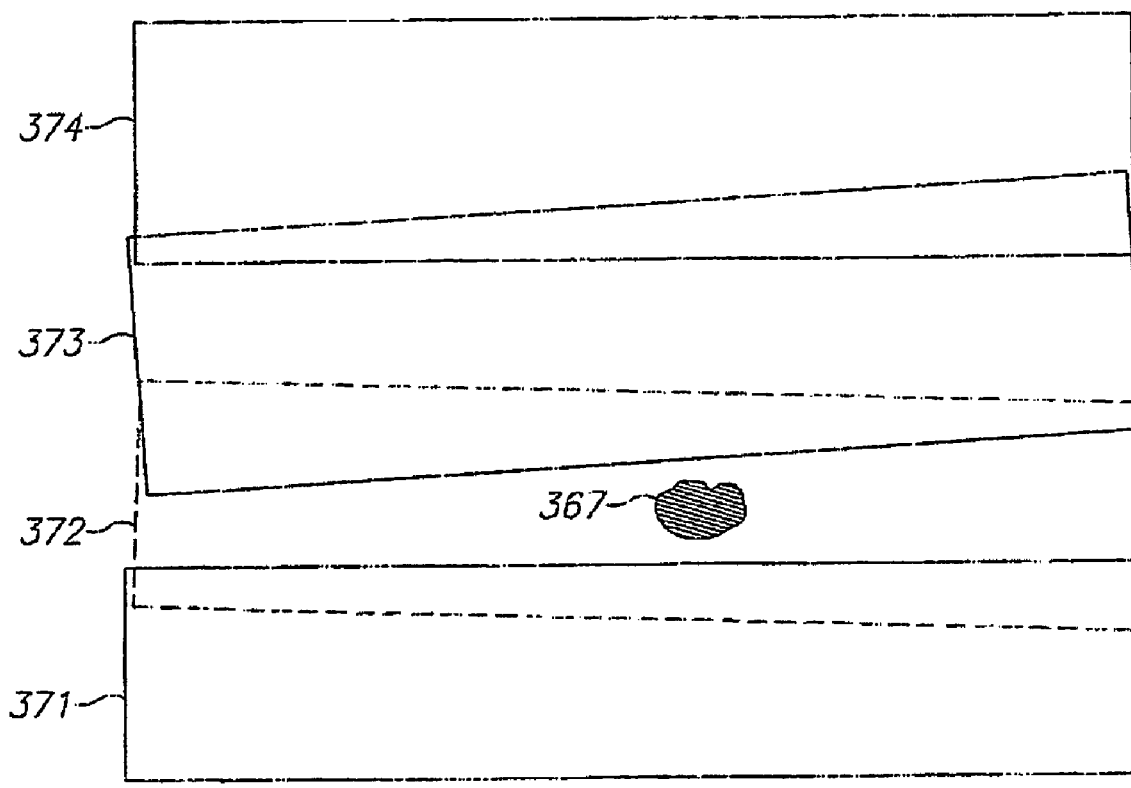

FIG. 3D schematically illustrates an alignment of images in accordance with some embodiments of the invention. For example, in one embodiment, the four images 361, 362, 363 and 364 of FIG. 3C may be processed, correlated and/or aligned, to produce four aligned images 371, 372, 373 and 374, respectively. It is noted that aligned image 372 may include, for example, the image of item 367.

Figure 3E:
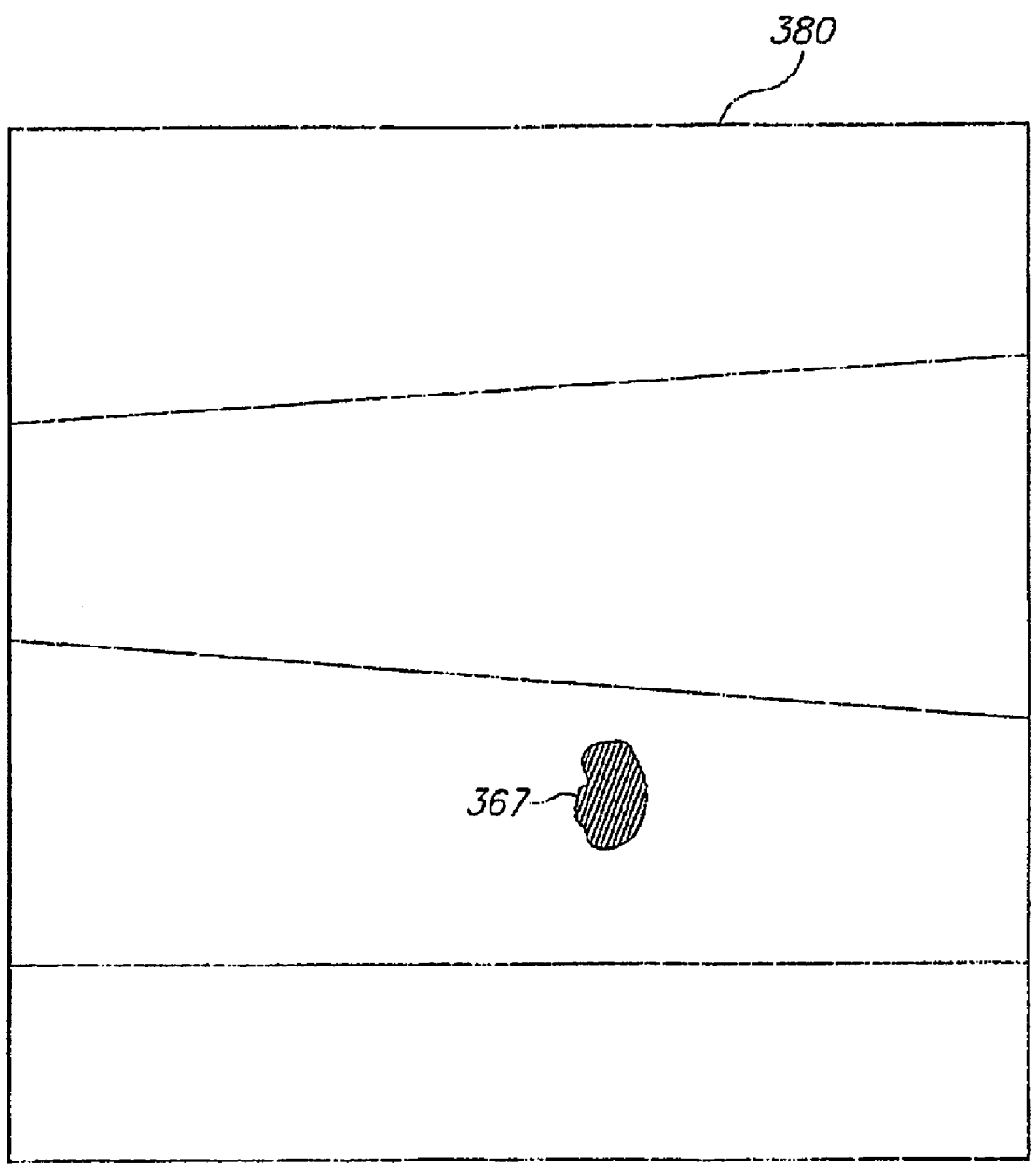

FIG. 3E schematically illustrates a combination of images in accordance with some embodiments of the invention. For example, in one embodiment, the four images 361, 362, 363 and 364 of FIG. 3C, and/or the four images 371, 372, 373 and 374 of FIG. 3D, may be processed, correlated and/or aligned, to produce a combined image 380. It is noted that combined image 380 may include, for example, the image of item 367.

It is noted that FIG. 3A to 3E include exemplary illustrations only, and that the present invention is not limited in this regard. In alternate embodiments, other suitable methods for capturing, converting, combining, matching, aligning, processing, correlating and/or displaying images may be used; for example, a relatively continuous "spiral" image or series of images may be captured and/or displayed, a discontinuous series of "slices" may be captured and/or displayed, etc. Images need not be combined or processed before display.

Figure 4A:
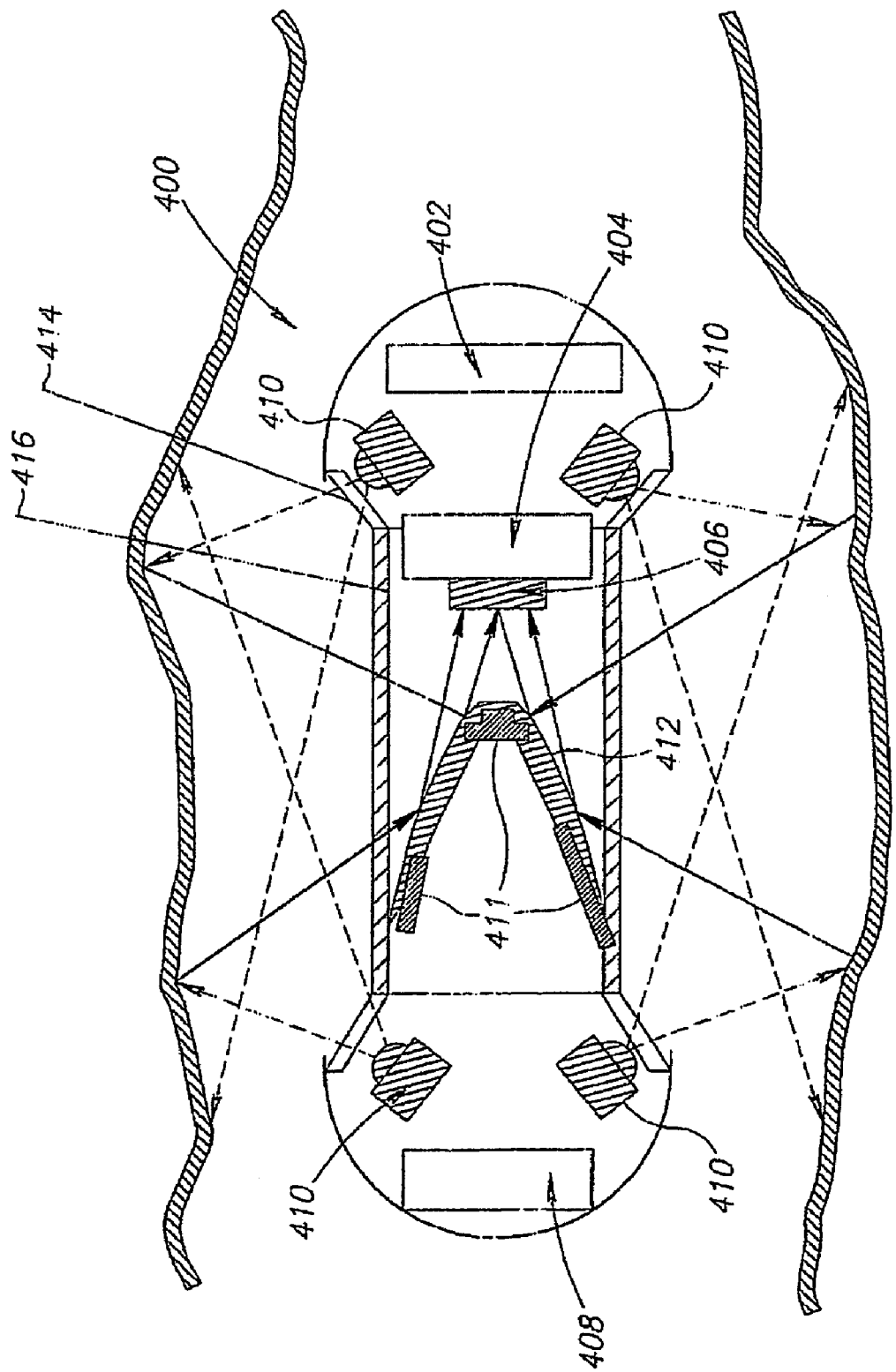
FIG. 4A is a schematic illustration of an in-vivo imaging device with a narrowed section in accordance with embodiments of the invention.

Reference is made to FIG. 4A, a schematic diagram of an in-vivo imaging device with a narrowed section in accordance with an embodiment of the invention with. Device 400 may include elements and/or may operate for example as described in FIG. 2 of this application. For example, device 400 may include a transmitter and an antenna 402, a processor 404, an image sensor 406, a power supply 408, one or more illuminators 410 and a reflective element such as for example a mirror 412 or a curved mirror. Mirror 412 may be held in place by for example anchors 411. Portions of for example an outer shell of device 400, such as for example a narrowed portion of device 400, may be transparent to the light emitted by illuminators 410. For example, section 414 of device 400 may be a transparent portion of an outer shell of device 400 in front of illuminator 410. Section 414 may allow light (indicated by dashed lines) emitted by illuminator 410 to exit device 400 and reach an endo-luminal area. Section 414 may be angled to form part of a tapered section between one or more wider ends of device 400 and a narrower transparent ring 416. In some embodiments the transparent ring 416 may be in the shape of a partial ring or a window or other shape. Transparent ring 416 may for example be transparent to the light emitted by illuminators 410 that is reflected back off of for example an endo-luminal wall (as indicated by solid lines) to device 400. According to one embodiment device 400 maintains a capsule like shape, which may be advantageous for movement in-vivo, however the transparent ring 416 may be configured such that an appropriate field of illumination of the body lumen walls may be achieved with a reduced risk of stray light or backscatter from illumination sources 410 onto the image sensor 406. Device 400 may in some embodiments capture a panoramic (such as for example 360 degrees) or partially panoramic view of an in-vivo area. According to one embodiment, illuminators 410 may be substantially contiguous with transparent section 414 and transparent ring 416 such that no or few light rays emitted from the illumination sources 410 are backscattered onto image sensor 406, but rather they are incident on the body lumen walls and can be reflected onto image sensor 406. According to one embodiment, illuminators 410 are positioned behind section 414 of transparent ring 416, which is typically beveled or at an angle to transparent ring 416, so as to enable an unobstructed field of illumination on the body wall being imaged, but so as not to obstruct light rays remitted from the body lumen wall onto the imager.

In some embodiments, an area of an imaging device 400 may be concave, tapered, narrowed or 'pinched' so that the device may have a shape resembling a peanut. Such concave area may for example include transparent ring 416, segment or viewing window through which light may enter and be reflected off of mirror 412 onto an image sensor 406. In some embodiments, mirror 412 may be in a parabolic shape, such that for example light rays striking mirror 412 from various directions will be reflected towards image sensor 406. In some embodiments, the peanut shape may minimize the backscatter light that reaches the image sensor 406 directly from illuminators 410 rather than after being reflected off of endo-luminal wall.

Figure 4B:
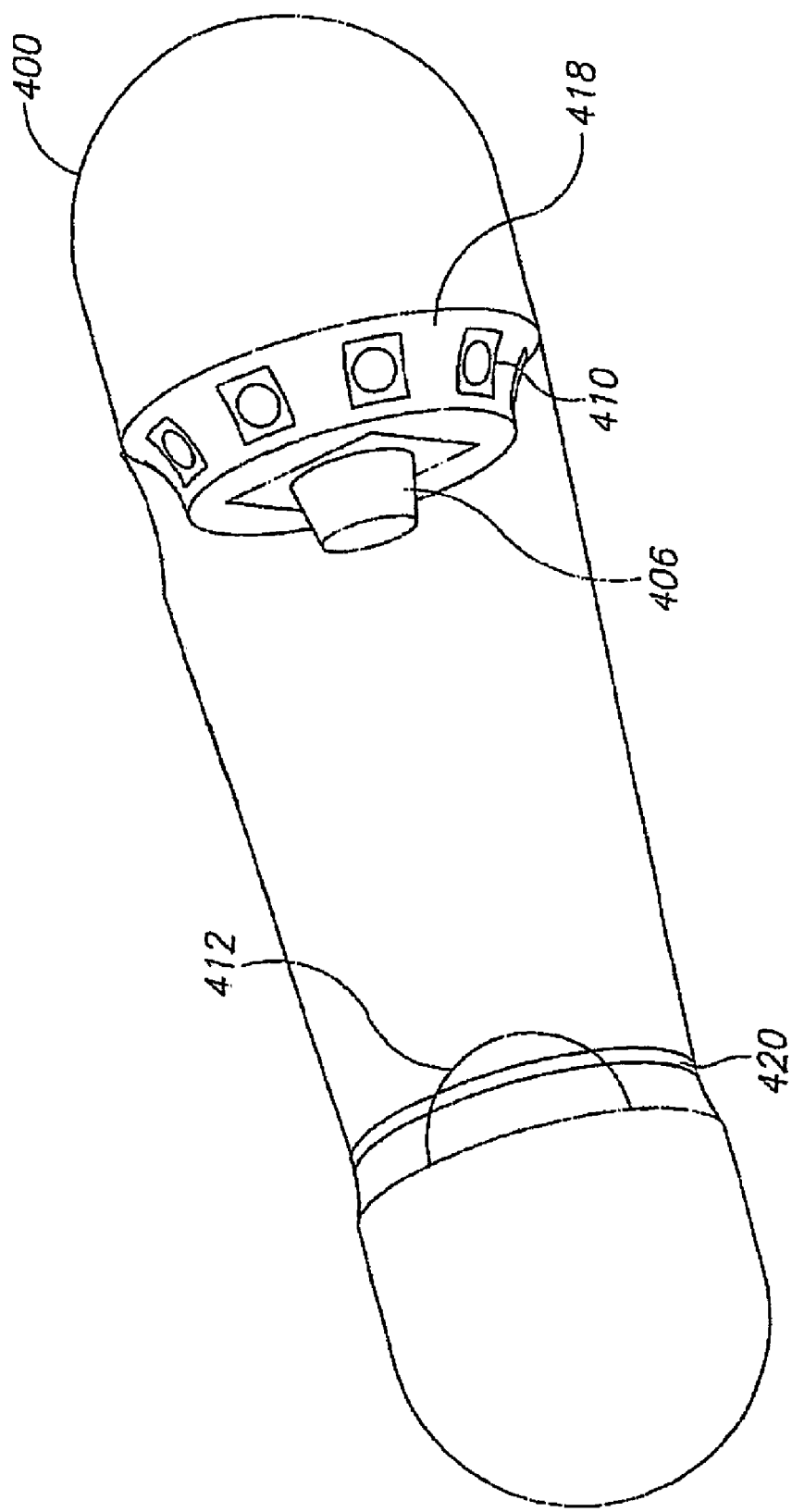
FIG. 4B is a schematic illustration of a series of light emitting diodes that are situated on a ring that is slanted outward in accordance with an embodiment of the invention.

Reference is made to FIG. 4B, a schematic diagram of a ring of light emitting diodes (LEDs) or illuminators 410 that may be on a ring that is slanted outward in relation to the plain of an image sensor 406 in accordance with an embodiment of the invention. Illuminators 410 may be situated for example on an outward facing ring 418 such that illuminators 410 face outward and away from image sensor 406. Placement of illuminators 410 on ring 418 as it is slanted outward and away from image sensor 406 may avoid backscatter of light directly from illuminators onto image sensor 406. In another embodiment, a second reflective element 420 may be situated behind mirror 412 so as to reflect onto an endo-luminal wall light that may be emitted directly from illuminators 410 and that might otherwise not reach endo-luminal wall.

Figure 5:
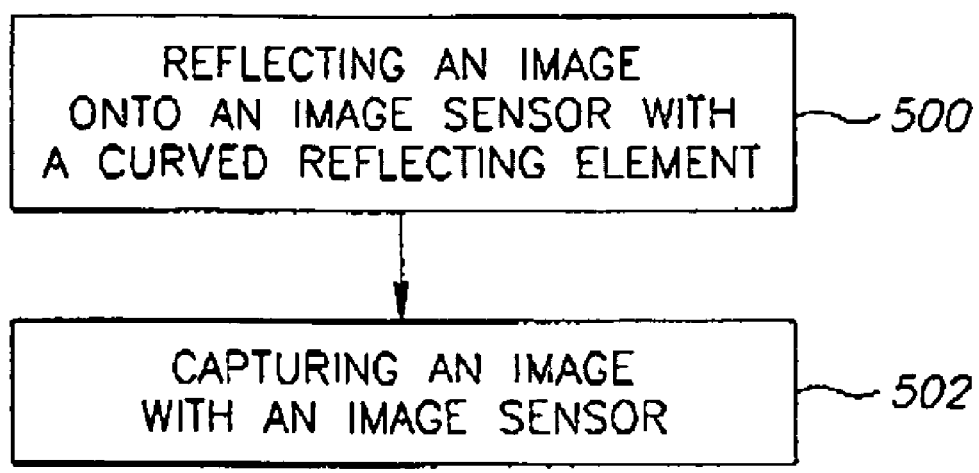
FIG. 5 is a flow chart diagram of a method of capturing an image using a curved reflective element in accordance with an embodiment of the invention.

FIG. 5 is a flow chart diagram of a method of capturing an image using a curved reflective element in accordance with embodiments of the invention. In one embodiment, device 200 may traverse body lumen 271. As is indicated in block 500, an image of an in-vivo area may be reflected onto an imager 46 or image sensor by way of a curved reflective element 260. In block 502 the reflected image may be captured by the imager 46. Imager 46 may capture images of portions of body lumen 271, for example, of slice 272.

The images may be processed and/or converted and/or combined, for example using processing unit 47 or, typically after transmission, using an external processor such as processor 14. As indicated at block 530, the images may be transmitted using transmitter 41 and antenna 48. Other transmission methods may be used.

The image may be received by receiver 12 and may be transferred to data processor 14. The image may be displayed and/or stored in storage unit 19.

Other operations of series of operations may be used. The above operations may be repeated as desired, for example, until a pre-defined period of time elapses, and/or until a pre-defined number of images are taken, and/or until the imaging device exits the patient's body, until a user instructs the system to discontinue repeating the above operations, and/or until another pre-defined condition and/or criteria are met.

Additionally or alternatively, if desired, a captured image or a plurality of captured images may be converted, for example, from a circular and/or ring shape into a rectangular shape. Additionally or alternatively, if desired, a plurality of captured images and/or converted images may be combined into one or more combined images of body lumen 271. The captured images, the converted images and/or the combined images may be displayed, for example, using monitor 18.

Additionally or alternatively other operations may be performed with the captured images, the converted images and/or the combined images, for example, to store such images using various types of storage devices, to print such images using a printer, to perform operations of image manipulation and/or enhancement, to perform operations of video manipulation and/or enhancement, or the like.

Figure 6:
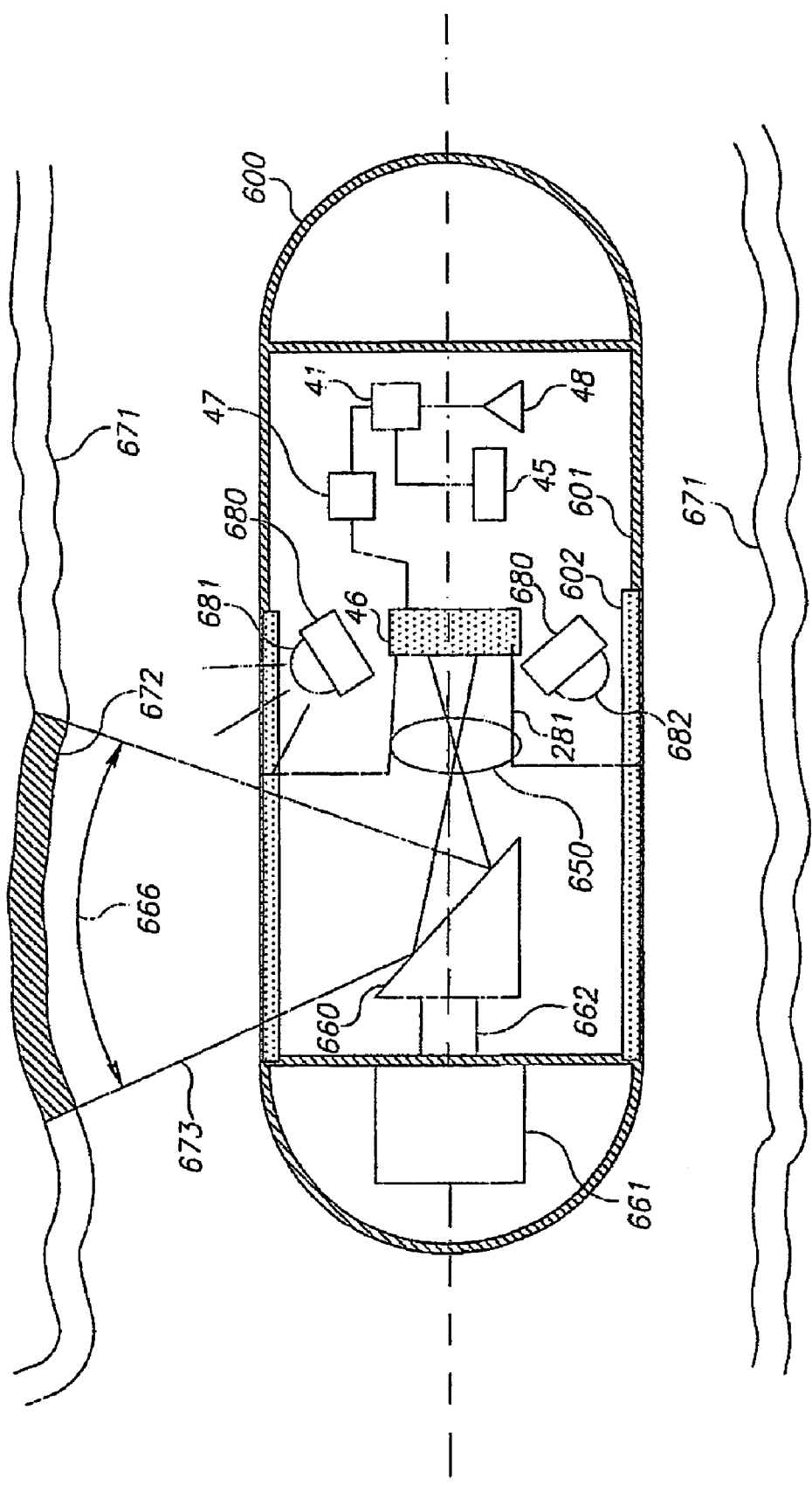
FIG. 6 is a schematic illustration of an in-vivo imaging device including a rotating mirror in accordance with embodiments of the invention.

FIG. 6 is a schematic illustration of an in-vivo imaging device 600 in accordance with embodiments of the invention. Device 600 may be an implementation or variation of device 40, and may be used, for example, in conjunction with the system of FIG. 1. For example, device 600 may be used in conjunction with receiver 12 and/or data processor 14. In one embodiment of the invention, device 600 may include a device 601, for example a capsule, an imager 46, a processing unit 47, a transmitter 41, an antenna 48, a power source 45, a lens assembly 650, a mirror or reflective device 660, one or more illumination sources 680, and a holder 281. Device 660 may further include a motor 661 and a shaft 662.

In one embodiment of the invention, device 600 may be a swallowable capsule. Device 600 may be partially or entirely transparent. For example, device 600 may include one or more areas and/or portions, such as a transparent shell or portion 602, which are transparent and which allow components inside device 600 to have an un-obstructed field-of-view of the environment external to device 600. In alternate embodiments, transparent areas and/or portion may have different shapes.

Lens assembly 650 may include, for example, one or more lenses or optical systems which allow images reflected by mirror 660 to be focused on imager 46. Additionally or alternatively, lens assembly 650 may include a combination of lenses able to zoom in and/or zoom out on an image or on several parts of an image reflected by mirror 660. Lens assembly 650 may include one or more optical elements, for example, one or more lenses and/or optical filters, to allow or to aid focusing reflected light onto imager 46 and/or performing other light processing operations.

Mirror 660 may include, for example, a glass and/or metal mirror or any other suitable reflective surface. Mirror 660 may be placed, positioned and/or aligned to allow a slice 672 or other portion of a body lumen 671 to be reflected by mirror 660, through lens assembly 650, onto imager 46. For example, mirror 660 may be situated at a 45 degree angle to the plane of imager 46 or to the plane of transparent shell 602. It is noted that other angles may be used to achieve specific functionalities and/or to allow imager 46 a broader or narrower field-of-view. Further, in some embodiments, other arrangements and/or series of optical elements may be used, and functionalities, such as reflecting and/or focusing, may be combined in certain units.

Illumination sources 680 may include one or more illumination sources or light sources to illuminate body lumen 671 and/or a slice 672 of body lumen 671. In one embodiment, illumination sources 680 may include one or more Light-Emitting Diodes (LEDs), for example, one or more white LEDs. Such LEDs may be placed, aligned and/or positioned to allow a desired illumination of body lumen 671, for example, using a ring-shaped arrangement of LEDs able to illuminate body lumen 671 through transparent shell 602.

Motor 661 may include an electro-mechanical motor able to rotate shaft 662 which may be attached to motor 661, and mirror or reflective device 660 which may be attached to shaft 662. The rotation rate of motor 661 may be constant or variable. The rotation rate of motor 661 may be, for example, 250 rotations per minute; other constant and/or variable rotation rates may be used. It is noted that when motor 661 rotates shaft 662 and mirror or reflective device 660, the field-of-view of imager 46 may change respectively, such that the instantaneous field-of-view 666 of imager 46 may include a part of slice 672 of body lumen 671. Additionally or alternatively, in one rotation of mirror 660, the field-of-view of imager 46 may include substantially an entire ring-shaped slice 672 of body lumen 671. Motor 661 may be controlled by, for example, transmitter 41; in alternate embodiments another unit such as a separate controller may provide such control.

In one embodiment, as device 600 traverses body lumen 671, device 600 may capture images of a slice of body lumen 671, such as slice 672. Illumination sources 680 may illuminate slice 672 of body lumen 671 when slice 672 is in the instantaneously field-of-view of imager 46. The light from illuminated slice 672 may be reflected using mirror or reflected surface 660, focused and/or transferred using lens assembly 650, and received by imager 46 which may thereby capture an image of slice 672. In alternate embodiments, other suitable methods for capturing images and/or displaying images may be used; for example, a relatively continuous "spiral" image or series of images may be captured, a discontinuous series of "slices" may be captured, etc.

In some embodiments, sets of illumination sources 680 may be turned on and/or turned off substantially simultaneously, such that substantially all illumination sources 680 are either turned on or turned off at a given point in time.

In other embodiments, some of illumination sources 680 are turned on and some of illumination sources 680 are turned off at a given point in time. For example, in one embodiment, illumination sources 680 may be configured to be in synchronization with rotation of motor 661 and/or mirror or reflective surface 660, such that the field of illumination created by illumination sources 680 creates sufficient light to illuminate the instantaneous field-of-view of imager 46

In some embodiments, illumination sources 680 may include a ring of light sources such as LEDs, for example, LEDs 681 and 682; some LEDs, for example, LED 681, may be turned on when other LEDs, for example, LED 682, are turned off, or vice versa. In one embodiment, illumination sources 680 may include a ring of LEDs, such that each LED may be synchronously on when the instantaneous field-of-view of imager 46 covers and/or overlaps the field of illumination of that LED. Of course, illumination sources other than LEDs may be used in accordance with embodiments of the invention.

In some embodiments, an optional optical system (not shown) may be used in conjunction with illumination source 680, for example, to create a desired illumination, for example, homogenous illumination, of an imaged body lumen. In one embodiment, the optical system may include, for example, one or more mirrors and/or curved mirrors and/or lenses and/or reflective elements, and/or filters shaped and/or positioned and/or aligned to create a desired, e.g., homogenous, illumination. For example, in one embodiment, the optical system may include a curved mirror, similar to reflective element 260 of FIG. 2.

In one embodiment, since device 600 may include transparent areas, such as transparent shell 602, the captured image may include a reflected image of a ring-shaped slice 672 of body lumen 271. It is noted that lens assembly 650 may be configured, placed and/or aligned to filter and/or focus light from body lumen 671, such that only light from a desired portion of body lumen 671, for example, a ring-shaped slice 672, falls on imager 46. Using device 600 may allow capturing a panoramic image of slice 672 of body lumen 671. Such panoramic image may include a substantially complete 360 degrees image of slice 672. Alternatively, if desired, such image may include a non-complete image of slice 672, for example, a 270 degrees image, a 180 degrees image, or other wide angle or partially panoramic images of a body lumen.

In one embodiment, the panoramic image of slice 672 may be ring-shaped. Such an image may be converted into a rectangular image of slice 672 or into other shapes as is described elsewhere in this application.

Images of slices of body lumen 671, such as slice 672, may be placed, aligned and/or combined together, for example, side by side, to create a combined image or several combined images from a plurality of images of slices. The combination of images of slices may be performed, for example, by processing unit 47 and/or data processor 14. Additionally or alternatively, the combination of images of slices may be performed before and/or after transmission of the image by transmitter 41 to receiver 12.]

In one embodiment, imager 46 may capture one or more images of body lumen 671 per rotation of motor 661. Other capture rates, constant or variable, may be used. In one embodiment, imager 46 may continuously remain active and/or receive light to take one image per rotation of motor 661.

In some embodiments, device 600 may further include one or more additional sets of imager and lens, to take images of other areas of body lumen 671 in addition to the images taken using imager 46. For example, device 600 may include an additional imager or several additional imagers (not shown), which may be positioned to obtain a field-of-view different (e.g, broader) from the field-of-view of imager 46. In some embodiments, imager 46 may include one or more imagers positioned to cover a broader field-of-view, for example, three or four imagers in a circular configuration aimed towards body lumen 671.

Figure 7:
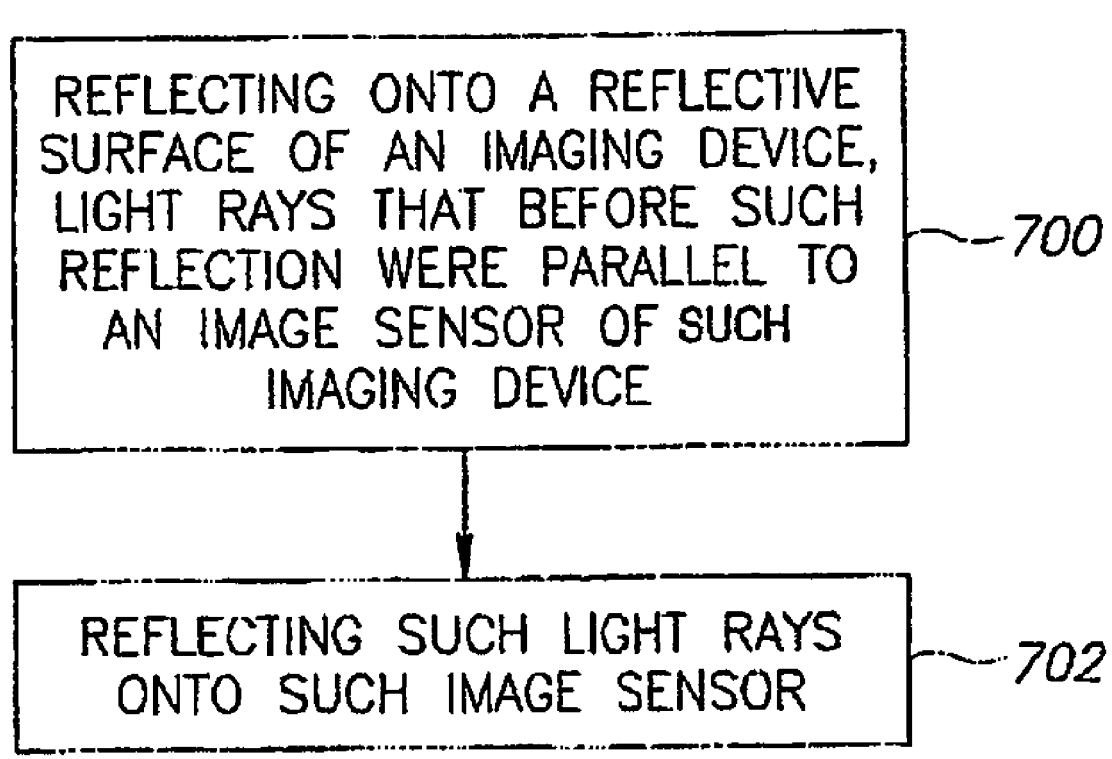
FIG. 7 is a flow chart of a method of reflecting onto an imager light rays that are substantially parallel to the imager, in accordance with embodiments of the invention.

Reference is made to FIG. 7, a flow chart of a method of reflecting light rays onto an imager 46 in accordance with an embodiment of the invention. In block 700, light rays 673 may be reflected onto a mirror or reflective device 660 of device 600. Some of such light rays 673 before such reflection may have been parallel or substantially parallel to a plane of an imager 46 of imaging device 600 upon which light detection sensors may be located. In block 702, the lights rays 673 may be reflected off of mirror or reflective surface 660 and onto imager 46. In an embodiment of the invention, mirror or reflective surface 660 may be situated at an angle, such as for example a 45 degree angle to the imager 46. Other angles may be used. In some embodiments, mirror or reflective surface 660 may be rotated by for example a motor 661, and there may be reflected onto imager 46 a panoramic or partially panoramic image of an in-vivo are surrounding the device 600. In some embodiments illumination sources 680 may direct light through a transparent portion of the imaging device onto an in-vivo area.

Figure 8:
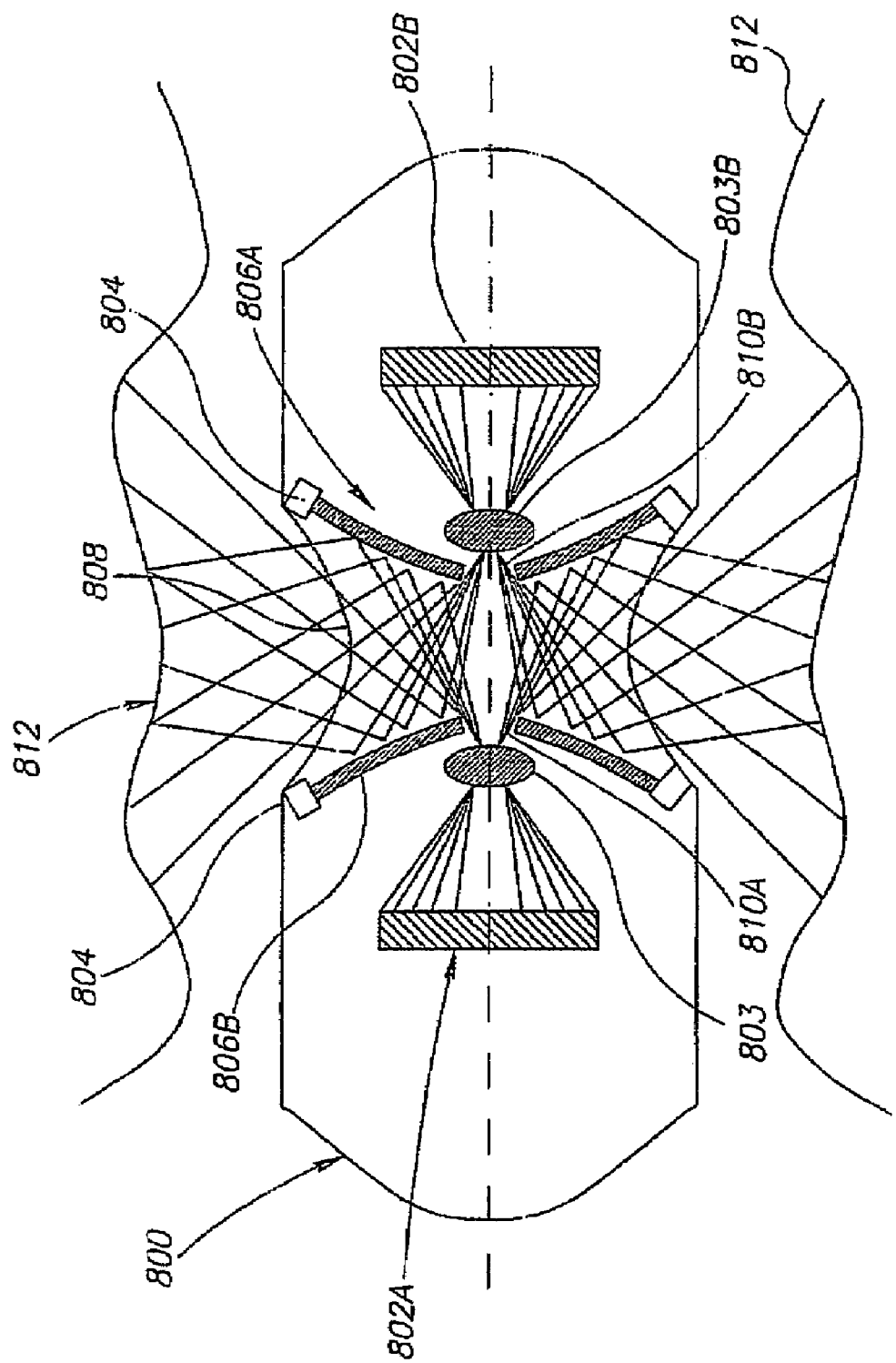
FIG. 8 is a depiction of a stereo panoramic in-vivo imaging device in accordance with an embodiment of the invention.

Reference is made to FIG. 8, a depiction of a stereo panoramic capsule in accordance with an embodiment of the invention. Device 800 may include a plurality of image sensors 802, a plurality of lenses 803, and a plurality of illumination sources 804. In some embodiments, a plurality of mirrors 806 such as for example curved mirrors or mirrors shaped in a parabolic from may be situated facing each other between a tapered section or concave ring 808 of the outer shell of device 800. One or more of lenses 803 may be situated behind an opening or space in mirrors 806 such that light reflected off of a mirror 806A passes through space 810A towards lens 802A, and light reflected off mirror 806B may pass through space 810B towards lens 803B. Device 800 may in some embodiments be suitable to capture a three dimensional and panoramic view of endo-luminal walls 812.

While some features are described in the context of particular embodiments, the invention includes embodiments where features of one embodiment described herein may be applied to or incorporated in another embodiment. Embodiments of the present invention may include features, components, or operations from different specific embodiments presented herein. While certain features of the invention have been illustrated and described herein, many modifications, substitutions, changes, and equivalents may occur to those of ordinary skill in the art. It is, therefore, to be understood that the appended claims are intended to cover all such modifications and changes as fall within the true spirit of the invention.

We claim:

1. An in-vivo imaging system comprising:
   an in-vivo imaging device comprising:
      an image sensor;
      a shell having a transparent ring around a perimeter of said shell and at least one end wider than said transparent ring, the shell further comprises a transparent tapered section between said wider end and said transparent ring;
      an illuminator positioned behind said tapered section;
      a curved reflective element to reflect onto said image sensor light reflected from an in-vivo area through said transparent ring towards said reflective element; and
      a transmitter;
   and
   an external receiver to receive images captured by said image sensor and transmitted by said transmitter.

2. The system as in claim 1, wherein said shell has a concave area.

3. The system as in claim 1, comprising a processor to combine a plurality of images captured by said imaging device into a continuous image.

4. The system as in claim 1, comprising a processor to change a circular image into a rectangular shaped image.

5. The system as in claim 1, wherein an outer surface of said shell has a concave area.

6. The system as in claim 5, wherein said concave area comprises said transparent ring.

7. The system as in claim 1, wherein said reflective element is situated at an angle to the plane of the image sensor.

8. The system as in claim 1, wherein said reflective element is shaped as a parabola.

9. The system as in claim 1, wherein said reflective element is selected from the group consisting of: a curved mirror, a metallic element, a reflective plastic element, a reflective coated plastic element and a glass element.

10. The system as in claim 1, comprising a motor to rotate said reflective element.

11. The system as in claim 1, wherein said illuminator is placed on a slanted ring such that the illuminator faces outward.

12. The system as in claim 1, wherein the device is a swallowable capsule.

* * * * *